US00PP33550P2

(12) United States Plant Patent
Wood

(10) Patent No.: US PP33,550 P2
(45) Date of Patent: Oct. 12, 2021

(54) ***CALYCANTHUS* PLANT NAMED 'SMNCAF'**

(50) Latin Name: *Calycanthus floridus*
Varietal Denomination: SMNCAF

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 17/039,867

(22) Filed: Sep. 30, 2020

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — C. Anne Whealy

(57) ABSTRACT

A new and distinct cultivar of *Calycanthus* plant named 'SMNCAF', characterized by its upright to somewhat outwardly spreading plant habit; moderately vigorous growth habit; strong lateral branches; freely branching habit, dense and bushy appearance; glossy leaves; freely flowering habit; fragrant dark red-colored flowers; and good garden performance.

2 Drawing Sheets

Figure 1:
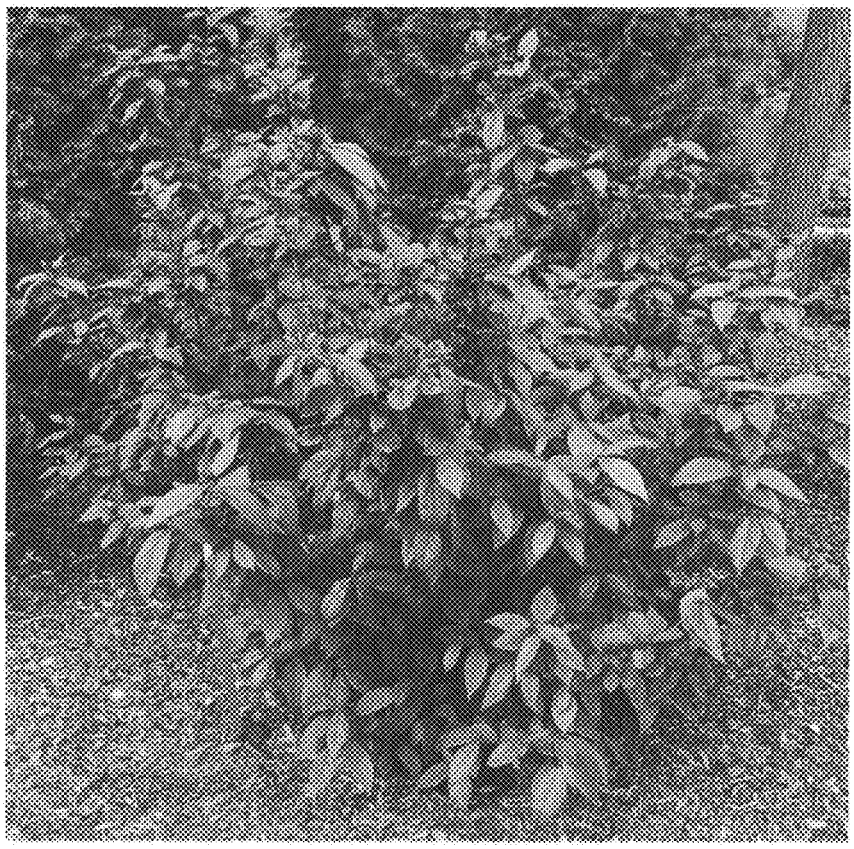

Botanical designation: *Calycanthus floridus*.
Cultivar denomination: 'SMNCAF'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Calycanthus* plant, botanically known as *Calycanthus floridus*, commonly referred to as Sweetshrub or Carolina Allspice and hereinafter referred to by the name 'SMNCAF'.

The new *Calycanthus* plant is a product of a planned breeding program conducted by the Inventor in Grand Haven, Mich. The objective of the breeding program was to create new upright and freely-branching *Calycanthus* plants with attractive foliage and fragrant flowers.

The new *Calycanthus* plant originated from an open-pollination in 2009 in Grand Haven, Mich. of an unnamed proprietary seedling selection of *Calycanthus floridus*, not patented, as the female, or seed, parent with an unknown proprietary selection of *Calycanthus floridus* as the male, or pollen, parent. The new *Calycanthus* plant was discovered and selected by the Inventor as a single plant within the progeny of the stated open-pollination in a controlled environment in Grand Haven, Mich. in 2012.

Asexual reproduction of the new *Calycanthus* plant by softwood stein cuttings in a controlled environment in Grand Haven, Mich. since 2012 has shown that the unique features of this new *Calycanthus* plant are stable and reproduced true to type in successive generations.

SUMMARY OF THE INVENTION

Plants of the new *Calycanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNCAF'. These characteristics in combination distinguish 'SMNCAF' as a new and distinct *Calycanthus* plant:

1. Upright to somewhat outwardly spreading plant habit.
2. Moderately vigorous growth habit.
3. Strong lateral branches.
4. Freely branching habit, dense and bushy appearance.
5. Glossy leaves.
6. Freely flowering habit.
7. Fragrant dark red-colored flowers.
8. Good garden performance.

Plants of the new *Calycanthus* differ primarily from plants of the female parent selection in plant habit as plants of the new *Calycanthus* are more uniform than plants of the female parent selection.

Plants of the new *Calycanthus* can also be compared to plants of *Calycanthus floridus* 'Michael Lindsey', not patented. In side-by-side comparisons, plants of the new *Calycanthus* differ primarily from plants of 'Michael Lindsey' in the following characteristics:

1. Plants of the new *Calycanthus* have larger flowers than plants of 'Michael Lindsey'.

2. Flowers of plants of the new *Calycanthus* are dark red in color whereas flowers of plants of 'Michael Lindsey' are orange red in color.
3. Flowers of plants of the new *Calycanthus* are more fragrant than flowers of plants of 'Michael Lindsey'.

BRIEF DESCRIPTION OF THE PHOTOGRAPHS

The accompanying colored photographs illustrate the overall appearance of the new *Calycanthus* plant showing the colors as true as it is reasonably possible to obtain in colored reproductions of this type. Colors in the photographs may differ slightly from the color values cited in the detailed botanical description which accurately describe the colors of the new *Calycanthus* plant.

The photograph on the first sheet (FIG. 1) is a side perspective view of a typical flowering plant of 'SMNCAF' grown in a outdoor nursery during the summer.

Figure 2:
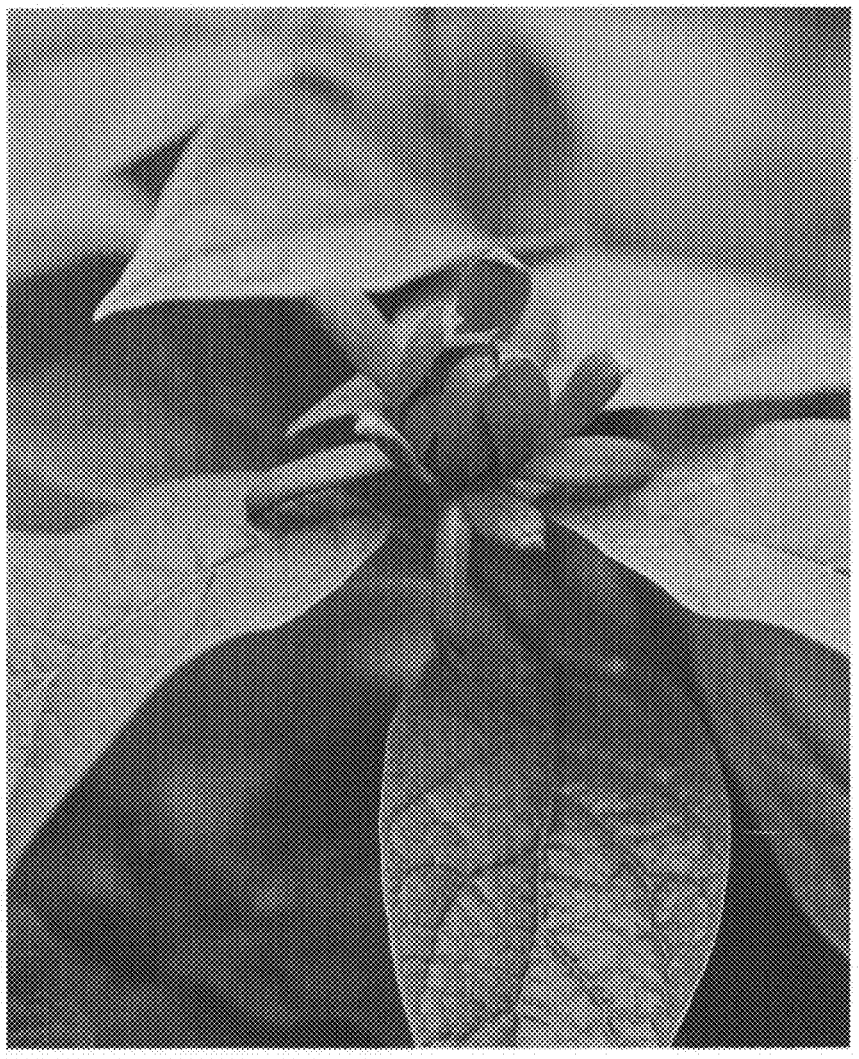

The photograph on the second sheet (FIG. 2) is a close-up view of a typical flowering plant of 'SMNCAF'.

DETAILED BOTANICAL DESCRIPTION

The following observations, measurements and values describe plants grown during the spring and summer in three-gallon containers in a polyethylene-covered greenhouse in Grand Haven, Mich. and under cultural practices typical of commercial production. Plants were two years old when the photographs and description were taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical classification: *Calycanthus floridus* 'SMNCAF'.

Parentage:

*Female, or seed, parent*.—Unnamed proprietary seedling selection of *Calycanthus floridus*, not patented.

*Male, or pollen, parent*.—Unknown proprietary selection of *Calycanthus floridus*, not patented.

Propagation:

*Type*.—By softwood stein cuttings.

*Time to initiate roots plant, summer*.—About four to six weeks at temperatures ranging from 18° C. to 27° C.

*Time to produce a rooted plant, summer*.—About three months at temperatures ranging from 18° C. to 27° C.

*Root description*.—Fine to thick, fibrous; typically white to brown in color, actual color of the roots is dependent on substrate composition, water quality, fertilizer, substrate temperature and physiological age of roots.

*Rooting habit*.—Freely branching; dense.

Plant description:

*Plant and growth habit*.—Deciduous perennial shrub; upright to somewhat outwardly spreading plant habit; dense and bushy appearance; moderately vigorous growth habit and rapid growth rate.

*Plant height*.—About 66 cm.

*Plant width* (*spread*).—About 59 cm.

*Lateral branches*.—Quantity: Freely branching habit with about ten primary lateral branches developing per plant; pinching enhances lateral branch development. Length: About 45 cm. Diameter: About 4 mm. Internode length: About 3 cm. Strength: Strong. Aspect: Erect to about 35° from vertical. Texture: Smooth, glabrous. Color: Close to 199C.

Leaf description:

*Arrangement*.—Opposite, simple.

*Length*.—About 12 cm.

*Width*.—About 4.5 cm.

*Shape*.—Oblanceolate.

*Apex*.—Acuminate.

*Base*.—Cuneate.

*Margin*.—Entire.

*Texture, upper surface*.—Rough, glabrous; glossy.

*Texture, lower surface*.—Slightly rough with prominent venation, mostly glabrous with pubescence along the veins.

*Venation pattern*.—Pinnate.

*Color*.—Developing and fully expanded leaves, upper surface: Close to 144A; venation, close to 145A. Developing and fully expanded leaves, lower surface: Close to 138A; venation, close to 145A.

*Petioles*.—Length: About 7.5 mm to 10 mm. Diameter: About 2 mm. Texture, upper and lower surfaces: Slightly pubescent. Color, upper surface: Close to 146B. Color, lower surface: Close to 145A.

Flower description:

*Flower type and flowering habit*.—Single axillary flowers with numerous ligulate petals and sepals, petals and sepals similar in shape and color; freely flowering habit with about 25 flowers per plant at one time; flowers face upright to outwardly.

*Fragrance*.—Fragrant, melon-like; pleasant.

*Natural flowering season*.—Plants flower during the late spring in Michigan.

*Flower longevity*.—Flowers last about two to three weeks on the plant; flowers not persistent.

*Flower buds*.—Height: About 1 cm. Diameter: About 8 mm. Shape: Ovoid. Color: Close to N186C.

*Flower diameter*.—About 6 cm.

*Flower depth*.—About 3 cm.

*Petals*.—Quantity per flower: Typically ten arranged in whorls. Length: About 1.5 cm. Width: About 4 mm. Shape: Ligulate. Apex: Acute. Base: Truncate. Margin: Entire. Aspect: Curling inwardly. Texture, upper and lower surfaces: Pubescent; coriaceous. Color: Developing petals, upper and lower surfaces: Close to 183A. Fully developed petals, upper and lower surfaces: Close to 183A; color does not change with development.

*Sepals*.—Quantity per flower: Typically ten arranged in whorls. Length: About 3 cm to 4 cm. Width: About 1 cm. Shape: Ligulate. Apex: Acute. Base: Truncate. Margin: Entire. Aspect: Outwardly spreading to reflexing. Texture, upper and lower surfaces: Pubescent; coriaceous. Color: Developing petals, upper and lower surfaces: Close to 183A. Fully developed petals, upper and lower surfaces: Close to 183A; color does not change with development.

*Peduncles*.—Length: About 1.5 cm. Diameter: About 3 mm. Strength: Strong. Angle: About 45° from vertical. Texture: Slightly pubescent. Color: Close to 144B.

*Reproductive organs*.—Stamens: Quantity per flower: Typically 20. Filament length: About 1 mm. Filament color: Close to 183B. Anther length: About 2 mm. Anther shape: Elliptical, curled inwardly. Anther color: Close to 160B. Pollen amount: Scarce.

Pollen color: Close to 160B. Pistils: Quantity per flower: Typically 15. Pistil length: About 1 mm to 2 mm. Style length: About 1 mm. Style color: Close to 183B. Stigma shape: Globose. Stigma color: Close to 200C. Ovary color: Close to 157A.

*Seeds and fruits*.—To date, seed and fruit development have not been observed on plants of the new *Calycanthus*.

Pathogen & pest resistance: To date, plants of the new *Calycanthus* have not been observed to be resistant to pathogens and pests common to *Calycanthus* plants.

Garden performance: Plants of the new *Calycanthus* have been observed to have good garden performance and tolerate rain, wind and to tolerate temperatures ranging from about −32° C. to about 36° C.

It is claimed:

1. A new and distinct *Calycanthus* plant named 'SMN-CAF' as illustrated and described.

* * * * *